United States Patent [19]

Hansen et al.

[11] Patent Number: 5,527,950
[45] Date of Patent: Jun. 18, 1996

[54] PROCESS FOR THE PREPARATION OF 5-FORMYLVALERATE

[75] Inventors: Carolina B. Hansen, Sittard; Antonius J. J. M. Teunissen, Geleen, both of Netherlands

[73] Assignees: DSM N.V., Heerlen, Netherlands; E.I. Du Pont de Nemours & Co., Wilmington, Del.

[21] Appl. No.: 365,478

[22] Filed: Dec. 28, 1994

[30]  Foreign Application Priority Data

Jan. 6, 1994 [BE] Belgium ............................... 09400008

[51] Int. Cl.⁶ ............................ C07C 67/36; C07C 69/66
[52] U.S. Cl. ........................ 560/175; 560/176; 560/177; 560/206; 568/454
[58] Field of Search ............................ 560/175, 176, 560/177, 206; 568/454

[56]  References Cited

U.S. PATENT DOCUMENTS

| Re. 31,812 | 1/1985 | Kuntz | 568/454 |
|---|---|---|---|
| 3,161,672 | 12/1964 | Zachry et al. | 260/486 |
| 3,253,018 | 5/1966 | Zachry et al. | 260/483 |
| 4,248,802 | 2/1981 | Kuntz | 568/454 |
| 4,287,369 | 9/1981 | Harris et al. | 568/454 |
| 4,360,692 | 11/1982 | Kummer et al. | 560/175 |
| 4,537,987 | 8/1985 | Schneider et al. | 560/193 |
| 4,567,306 | 1/1986 | Dennis et al. | 568/455 |
| 4,730,041 | 3/1988 | Hutmacher et al. | 540/538 |
| 4,748,261 | 5/1988 | Billig et al. | 556/404 |
| 4,801,738 | 1/1989 | Schneider et al. | 560/177 |
| 4,894,474 | 1/1990 | Maerkl et al. | 560/206 |
| 4,910,328 | 3/1990 | Bertleff et al. | 560/177 |
| 4,931,590 | 6/1990 | Kummer et al. | 562/590 |
| 5,003,102 | 3/1991 | Bertleff et al. | 560/177 |
| 5,202,297 | 4/1993 | Lorz et al. | 502/106 |
| 5,235,113 | 8/1993 | Sato et al. | 568/454 |
| 5,254,741 | 10/1993 | Lorz et al. | 568/454 |
| 5,264,616 | 11/1993 | Roeper et al. | 560/175 |

FOREIGN PATENT DOCUMENTS

| 20016285 | 10/1980 | European Pat. Off. . |
|---|---|---|
| 10060523 | 9/1982 | European Pat. Off. . |
| 20149894 | 7/1985 | European Pat. Off. . |
| 10301450 | 2/1989 | European Pat. Off. . |
| 1-450577 | 10/1991 | European Pat. Off. . |
| 10472071 | 2/1992 | European Pat. Off. . |
| 20518241 | 12/1992 | European Pat. Off. . |
| 12627354 | 12/1976 | Germany . |
| 283284 | 1/1965 | Netherlands . |
| 9303839 | 3/1993 | WIPO . |

Primary Examiner—José G. Dees
Assistant Examiner—Rosalynd A. Williams
Attorney, Agent, or Firm—Cushman Darby & Cushman

[57]  ABSTRACT

The invention relates to a process for the preparation of a 5-formylvalerate ester by hydroformylating a mixture of pentenoate esters in the presence of a catalyst system which catalyst system comprises a metal from group 8–10 of the Periodic Table of Elements and a mono- or multidentate organic phosphorous ligand, wherein the mixture of pentenoate esters contains less than 500 ppm hydroperoxide compounds.

16 Claims, No Drawings

PROCESS FOR THE PREPARATION OF 5-FORMYLVALERATE

FIELD OF THE INVENTION

The invention relates to a process for the preparation of a 5-formylvalerate ester by hydroformylating a mixture of pentenoate esters in the presence of a catalyst system in which the catalyst system comprises a metal selected from groups 8–10 of the Periodic Table of Elements and a mono- or multidentate organic phosphorous ligand.

BACKGROUND OF THE PRESENT INVENTION

A similar process is described in U.S. Pat. No. 5,264,616. U.S. Pat. No. 5,264,616 discloses a process for the preparation of an alkyl 5-formylvalerate starting from alkyl 4-pentenoate, alkyl 3-pentenoate or mixtures of alkyl 2-, 3- and 4-pentenoate in the presence of a catalyst system comprising rhodium (Rh) and a bidentate phosphite ligand.

A disadvantage of this process is that the activity of the catalyst system is low. Moreover the activity of the catalyst system decreases when the catalyst system is reused several times. The lower activity and stability of the catalyst system is especially found when the mixture of pentenoate esters contains (even small amounts of) cis 2-pentenoate ester.

SUMMARY AND OBJECTIONS OF THE PRESENT INVENTION

The object of this invention is therefore a process for the preparation of 5-formylvalerate ester by a hydroformylation starting from a mixture of pentenoate esters in which the activity of the catalyst system is high and will remain high for a prolonged period of time.

The object of the present invention is achieved in that the mixture of pentenoate esters contains less than 500 ppm hydroperoxide compounds.

DETAILED DESCRIPTION OF THE PRESENT INVENTION

The process of the present invention involves preparing a 5-formylvalerate ester by hydroformylating a mixture of pentenoate esters in the presence of a catalyst system, wherein the mixture of pentenoate esters contain less than 500 ppm of hydroperoxide compounds and the catalyst system comprises a metal from groups 8–10 of the periodic system and a ligand containing a mono- or multidentate organic phosphorous ligand.

The process according to the invention is preferably carried out with a pentenoate ester mixture containing less than 100 ppm and most preferably less than 50 ppm hydroperoxide compounds.

It has been found that, with the process according to the invention, the catalyst's activity is improved and that the catalyst remains stable for a longer period of time when starting with a mixture of pentenoate esters. A further advantage is that the selectivity for 5-formylvalerate is improved in a number of cases. The above advantages are even more pronounced if the process to prepare 5-formylvalerate ester is performed continuously in which the unconverted pentenoate ester of the process are reused as starting compounds of the hydroformylation. In a continuous process catalyst stability and activity are important factors.

The hydroperoxide compounds have proved to be catalyst poisons inasmuch as these compounds readily convert the organic phosphorous ligands into catalytically inactive compounds. These pentenoate ester compounds and especially cis-2-pentenoate ester were not heretofore known to "spontaneously" form hydroperoxide compounds when treated in the normal manner. It has also been found that in a mixture of pentenoate esters comprising cis 2-pentenoate ester an even higher amount of hydroperoxide compounds can be present. The formation of hydroperoxide compounds may be explained by the reaction of one or more of the pentenoate esters with traces of oxygen. The formation of hydroperoxide compounds was unexpected and especially the rapid formation of hydroperoxide compounds when cis 2-pentenoate ester was present was unexpected. This is surprising because it would be more logical that 3-pentenoate ester, having two allyl hydrogen groups capable of autooxidation to a hydroperoxide group, would be the more reactive compound. Even very small amounts of cis 2-pentenoate (smaller than 0.5 wt. % relative to the pentenoate mixture) in a pentenoate ester mixture have been found to cause a rapid formation of hydroperoxide compounds in which the hydroperoxides formed from the cis 2-pentenoate subsequently promote the formation of hydroperoxide compounds originating from other pentenoates for example 3-pentenoate ester. The formation of hydroperoxide compounds may take place due to infiltration of small amounts of oxygen (air) in the various process equipment present in a commercial hydroformylation process or due to the fact that the compounds used in the various chemical steps contain small traces of oxygen. Examples of process equipment are distillation column(s) for separation of the unconverted alkyl pentenoates or the process equipment of a possible previous step in which the pentenoate ester mixture is prepared.

The hydroperoxide compounds which are formed can be represented by the following formulas:

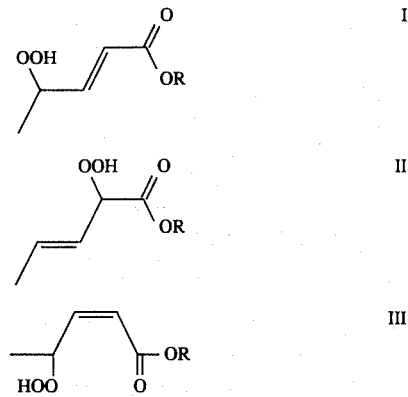

Unlike for ether compounds, as described in for example EP-A-60523, it is surprising that pentenoate esters readily form hydroperoxides. Ester compounds are not known to readily form hydroperoxides, in contrast with ether compounds, which are known to readily form hydroperoxide compounds. Especially for cis 2-pentenoate ester the hydroperoxide formation was not to be expected as explained above.

The process according to the invention can be carried out in a variety of embodiments. All embodiments will aim to prevent the hydroperoxide compounds from being formed or from reacting with a significant amount of phosphorous ligands during hydroformylation or during the possible subsequent separation stages. To achieve this it is important that during hydroformylation the concentration of hydroperoxide compounds should be as low as possible. In some cases, if the cost of (substantial) removal of the hydroperoxide compounds is higher than the economic losses resulting from the lower activity and stability of the catalyst system, it may be acceptable for a small amount of hydroperoxide compounds (< 500 ppm) to be present during hydroformylation or in the pentenoate ester mixture applied. When applying more expensive phosphorous ligands lower hydroperoxide concentrations are preferred.

In a first embodiment, the formation of hydroperoxide compounds in the pentenoate ester mixture applied is prevented by carrying out the various operations in the absence of oxygen during and starting from the preparation of the pentenoate ester and until the pentenoate ester is used in the hydroformylation step and when recycling the unconverted pentenoate ester to be used as starting compound of the process according to the invention.

In a commercial process whereby the pentenoate ester is prepared in a first step by, for instance, carbonylation of butadiene, the presence of oxygen in and after this first step will need to be avoided as much as possible in order to ensure that the content of hydroperoxide compounds remains low. It has been found that a small amount of oxygen can within a short period of time convert sufficient pentenoate esters into an amount of hydroperoxide compounds causing the aforementioned adverse effects in the hydroformylation.

In a second and more preferred embodiment the pentenoate ester-containing feed is substantially freed (in a separate operation) of hydroperoxide compounds. This is because it is not so easy to store and/or handle the pentenoate ester mixture with complete exclusion of oxygen since the pentenoate ester may come into contact with oxygen so that hydroperoxide compounds may occasionally form. Oxygen can for example come into contact with the pentenoate ester mixture via leaky gaskets of a commercial continuous process. These (occasionally occurring) high concentrations of hydroperoxide compounds will disturb the hydroformylation process and hamper smooth, continuous operation. Furthermore, it may be more practicable to free the pentenoate of hydroperoxide compounds in a separate operation than to prevent hydroperoxide formation as described above.

The process to free the pentenoate ester mixture from hydroperoxide compounds may be any operation known to one skilled in the art for removing hydroperoxide compounds. An example of a possible process comprises passing the hydroperoxide compounds-containing pentenoate ester over ordinary activated (dry) alumina at room temperature, causing the hydroperoxide compounds to decompose and/or to remain on the alumina. The contacting with alumina can advantageously be performed in a continuous process. The alumina is then preferably placed in a packed bed reactor.

Another example for removing hydroperoxide compounds is to distil the pentenoate in the presence of a phosphorous (III) containing compound, which as a rule is readily obtainable. This phosphorous compound will as a rule costs only a fraction of the price of the phosphorous ligand applied in the hydroformylation process. The hydroperoxide compounds will react with this phosphorous compound, as a result of which the concentration of hydroperoxide compounds will decrease.

Another example of removing the hydroperoxide compounds is to wash the organic pentenoate ester mixture with an aqueous mixture containing a water soluble phosphorous (III) compound. Such a method can be advantageously performed in a continuous manner, in which the aqueous mixture can be separated from the pentenoate ester mixture after contacting by phase separation. The aqueous phase can be reused for a next treatment of hydroperoxide containing pentenoate ester mixture.

Possible water soluble phosphorous compounds are sulfonated triphenylphosphine and sulfonated triphenylbisphosphine. Instead of water other solvents may also be applied in which the phosphorous compound will dissolve and which solvent can be separated from the pentenoate ester mixture by phase separation.

In case the pentenoate ester is stored for some time, the formation of hydroperoxides is prevented by keeping the pentenoate in the presence of a suitable radical scavenger or reducing agent. Examples of such reducing agents are dialkylthiodiproprionates, $((RO_2CCH_2CH_2)_2S$ in which R may be a $C_1$–$C_6$ alkyl) and aryl and alkyl monodentate phosphite compounds. Examples of suitable radical scavengers are phenols such as 2,4,6-tri-tert-butylphenol, tert-butyl-catechol and 2,6-di-tert-butyl-4-methylphenol.

The pentenoate ester according to the invention may be represented by the following general formula (IV):

$$R^1-C-O-R^2 \qquad (IV)$$
$$\underset{O}{\|}$$

where $R^1$ represents a linear butenyl group and $R^2$ an alkyl group having from 1 to 12 carbon atoms or an aryl group or an aralkyl group having from 6 to 12 carbon atoms. Preferably, $R^2$ is an alkyl group having from 1 to 8 carbon atoms for example methyl, ethyl, propyl, isopropyl, tert-butyl, isobutyl or a cyclohexyl or a phenyl group or benzyl group. Most preferably, $R^2$ is methyl, ethyl or phenyl.

The mixture of pentenoate esters will generally consist of esters with the same ester group ($R^2$). The group $R^1$ will mostly differ in this mixture. The mixture of pentenoate esters can in principle be any mixture of 2-, 3- and/or 4-pentenoate ester. The advantages of the invention are especially pronounced if the mixture contains cis 2-pentenoate ester. It has been found that cis 2-pentenoate esters form hydroperoxide compounds more readily than other isomeric pentenoate esters (for example 3-pentenoate ester and trans 2-pentenoate). The percentage of cis 2-pentenoate ester calculated on the total amount of pentenoate ester can be very small (0.01%). The mixture will as a rule consist mainly of 3-pentenoate ester and 4-pentenoate ester and their total concentration in the mixture will be between 50 and 100% while the remaining part is 2-pentenoate ester (trans+ cis). In a continuously operated preparation of 5-formylvalerate ester, in which the unconverted pentenoate ester is returned to the hydroformylation stage, the concentration of cis 2-pentenoate ester may be between 0.01 and 10%.

The invention particularly relates to a process starting from a mixture of pentenoates (2-, 3- and 4-pentenoates) that are prepared by carbonylating butadiene by a reaction with carbon monoxide, a hydroxy compound (for example methanol) and with a suitable carbonylation catalyst.

The hydroformylation catalyst system to be used in the process of the invention comprises of a metal from groups 8–10 of the Periodic Table of Elements (new IUPAC notation, Chemical and Engineering News, 63(5), 27, 1985) and an organic phosphorous ligand. The metal of group VIII is for example Co, Ru, Rh, Pd, Ir or Pt. The metal and the ligand are capable of forming a complex in the reaction mixture. The advantages of the invention are especially pronounced when the hydroformylation is performed with a catalyst system in which the bond between the ligand and the metal in the ligand-metal complex is not a strong one ('weak bond'). These catalysts systems are preferred because high selectivity and/or yield to 5-formylvalerate esters may be obtained when these catalyst systems are used in the process according to the invention. It has been found that such "weak bond catalyst systems" are more sensitive (with respect to activity, stability and/or selectivity) to the presence of hydroperoxide compounds than catalyst systems consisting of complexes with a stronger bond. These 'weak bond catalyst systems' are characterized in that the ligand of the ligand-metal complex is regularly exchanged in the reaction mixture with another ligand. As a rule, these catalyst systems are characterized by a large excess of ligand relative to the metal at optimal hydroformylation conditions. As a rule the ligand/metal molar ratio is greater than 2:1. Ratio's of 1000:1 are also possible. Familiar examples of catalyst systems of which the complexes formed are known to have a 'weak' bond are catalyst systems with ruthenium, cobalt, iridium and rhodium as the metal. Examples of rhodium-based catalyst systems are described in U.S. Pat. No. 4,801,738, EP-A-149,894, PCT Int'l. WO-A-9426688, and EP-A-472,071.

The process of the invention particularly relates to those catalyst systems with which, starting from a pentenoate ester mixture containing at least 20% 3-pentenoate ester, the corresponding 5-formylvalerate can be prepared with a selectivity greater than 65% at a realistic or practicable conversion and reaction rate. The phosphorous ligand of the hydroformylation catalyst may have monodentate or multidendate structures. The invention is especially suitable when catalyst systems are used comprising multidentate phosphorous ligands because these ligands are in most cases less easy to prepare. The advantage of an improved catalyst stability will be then even more pronounced.

The ligands are phosphorous-containing organic compounds in which the phosphorous group may be present in the molecule as a phosphine, phosphonite, phosphinite, phosphite and/or phosphorous amide group. Ligands with only one kind or different kinds of these phosphorous groups are possible.

The phosphorous ligand may for example be represented by the following chemical formula:

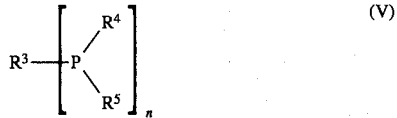
(V)

wherein n is 1–6. When n=1: $R^3$, $R^4$ and $R^5$ are the same or different monovalent organic groups selected from —Y, —O—Y, —N($R^6$)—Y or —S—Y or $R^4$ and $R^5$ form one divalent organic group —Y—, —O—Y—O—, —O—Y—, —O—Y—N($R^6$)— or —N($R^6$)—Y—N($R^7$)— and $R^3$ is a monovalent group as defined above and in which Y is a monovalent or divalent organic group with 1–20 carbon atoms and $R^6$ and $R^7$ are individually hydrogen or an organic group with 1 to 12 carbon atoms. When n is 2–6: $R^3$ is a multivalent organic bridging group with 1–30 carbon atoms and $R^4$ and $R^5$ can be the same or different monovalent groups as defined above and/or $R^4$ and $R^5$ form one divalent group as defined above.

Preferred phosphorous ligands are (a) monodentate compounds (n= 1) in which $R^3$, $R^4$ and $R^5$ are the following same or different monovalent organic groups: —Y or —O—Y or $R^4$ and $R^5$ form one divalent organic group in which divalent organic group is —Y— or —O—Y—O— and (b) multidentate compounds (n is 2–6) in which $R^3$ is a multivalent organic bridging group with 1–30 carbon atoms and $R^4$ and $R^5$ can be the same or different monovalent groups —Y or —O—Y and/or $R^4$ and $R^5$ form one divalent organic group in which the divalent organic group is: —Y— or —O—Y—O—.

Examples of possible monovalent groups Y are substituted or unsubstituted $C_6$–$C_{20}$ aryl or aralkyl groups, for example phenyl, naphthyl or benzyl; or $C_1$–$C_{20}$ alkyl groups for example methyl, ethyl, propyl, isopropyl, tert-butyl, pentyl or cyclohexyl. Examples of possible divalent groups Y are substituted or unsubstituted $C_1$–$C_{10}$ methylene groups, for example ethylene, trimethylene, tetramethylene or pentamethylene; or $C_6$–$C_{20}$ divalent arylene groups, for example divalent dinaphthyl or diphenyl.

Examples of multivalent bridging groups $R^3$ are multivalent groups having the formula $(X—)_n$ or $X—(O—)_n$ with n is 2–6. An example of a multidentate bridging group with n=4 is the tetravalent bridging group $C—(CH_2—O—)_4$. Examples of divalent bridging groups are —X—, —O—X—O—, —N($R^6$)—X— N($R^7$)— or —O—X—N($R^6$)— in which X is a divalent organic group with 1–30 carbon atoms. Preferably the bidentate bridging group is —X— or —O—X—O—. Examples of possible divalent groups X are substituted or unsubstituted $C_1$–$C_{10}$ alkylidene group, for example ethylene, trimethylene, tetramethylene and pentamethylene or trans-1,2-cyclobutene; or $C_6$–$C_{20}$ divalent arylene groups, for example divalent dinaphthyl or diphenyl; or 1,1'-ferrocenyl.

$R^6$ and $R^7$ may individually be for example hydrogen, $C_1$–$C_{11}$ alkyl group, for example methyl, ethyl or propyl, an aryl group, for example phenyl, tolyl or tosyl.

Groups X, Y, $R^6$ and $R^7$ may be substituted with organic groups with 1–10 carbon atoms or with anorganic groups, for example halogenide groups, for example Cl, Br or I. Examples of other anorganic and organic groups are nitro, cyano, trifluoromethyl, hydroxy, carbonyloxy, sulfonyl, sulfinyl, thionyl, silyl, alkoxy or thionyl.

Most preferably the ligand is a phosphite ligand with $X—(O—)_n$, —O—Y and/or —O—Y—O— groups in which n is 2–6 or a phosphine ligand with $(X—)_n$, —Y and/or —Y— groups with n is 1–6, in which X and Y are groups as defined above.

Examples of monodentate ligands are triarylphosphine and triarylphosphite.

Examples of bidentate phosphine ligands are 1,3-bis-(diphenylphosphino)propane, 1,4-bis(diphenylphosphino)butane, 2,3-dimethyl-1,4-bis(diphenylphosphino)butane, 1,4-bis(dicyclohexylphosphino)butane, 1,3-bis(di-p-tolylphosphino)propane, 1,4-bis(di-p-methoxyphenylphosphino)butane, 2,3-bis(diphenylphosphino)- 2-butene, 1,3-bis(diphenylphosphino)-2-oxopropane, 2-methyl-2-(methyldiphenylphosphino)-1,3-bis(diphenylphosphino)propane, 2,2'-bis(diphenylphosphino)biphenyl, 2,3-bis-(diphenylphosphino)-naphthalene, 1,2-bis(diphenylphosphino)-cyclohexane, 2,2'dimethyl-4,5-bis(diphenylphosphino)-dioxolane, 1,1'-bis(diphenylphosphino)-ferrocene, 1,1'-bis(diisobutylphosphino)-ferrocene, 1,1'-bis(diisopropylphosphino)-ferrocene, 1,1'-bis(dicyclohexylphosphino)-ferrocene, 1,1'-bis(isopropylcyclohexylphosphino)-ferrocene, 1,1'-bis(di-t-butylphosphino)ferrocene, 1-(diisopropylphosphino)- 1'-(phenylisopropylphosphino)ferrocene, 1-(diphenylphosphino)- 1'-(diisopropyl-phosphino)ferrocene, 1,1'-bis(isopropylphenylphosphino)ferrocene, 2,3-o-isopropylidene- 2,3-dihydroxy-1,4-bis(diphenylphosphino)butane (DIOP), trans-1,2-bis(di(m-methylphenyl)phosphinomethyl)cyclobutane, trans-[(bicyclo[2.2.1]- heptane- 2,3-diyl)bis(methylene)]-bis[diphenylphosphine], trans-[(bicyclo[2.2.2octane-2,3-diyl)bis(methylene)]bis[diphenylphosphine], trans-1,2-bis(diphenylphosphinomethyl)cyclobutane (DPMCB), trans-1,2-bis(diphenyl-phosphinomethyl)trans- 3,4-bis(phenyl)cyclobutane and 2,2'-bis(diphenylphosphino)-1,1'-binapthyl (BINAP).

Examples of possible bidentate phosphite ligands are the bidentate phosphite ligands described in U.S. Pat. No. 5,264,616. An example of such a bidentate phosphite ligand is given in formula (VI).

Formula (VI):

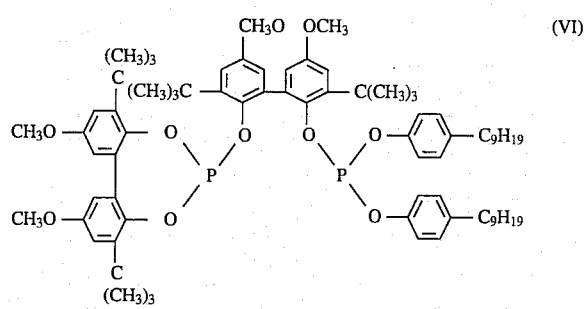

(—$C_9H_{19}$ = a linear $C_9$-alkyl group)

Examples of multidentate phosphorous ligands with 2 and more phosphorous groups are the multidentate phosphite ligands described in EP-A-518,241. An example of such a multidentate phosphite ligand is represented by Formula (VII).

Formula (VII):

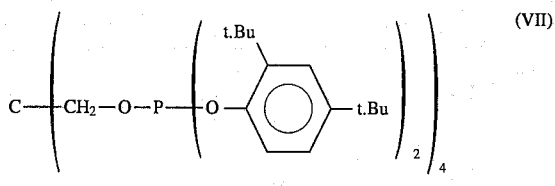

(t.Bu = tert-butyl group)

An example of a process which can be improved with the process according to the invention is described in PCT Int'l. WO-A-942668. This patent specification describes the preparation of 5-formylvalerate ester by using a rhodium-based catalyst system comprising rhodium and a triphenylphosphine, wherein the phenyl groups are modified with, for example, sulphonate groups. The following catalyst systems are examples of catalyst systems which may also advantageously be used, in the process according to the invention. An example of a hydroperoxide sensitive catalyst system comprises rhodium and a bidentate phosphorous ligand (such as for example the phosphite according to formula VI) and is described in U.S. Pat. No. 4,748,261. Another examples of catalyst system are the rhodium based catalyst systems as described in EP-A-518,241. EP-A-518,241 describes a hydroformylation catalyst system based on rhodium and a phosphite ligand (such as for example the phosphite according to formula VII).

The 5-formylvalerate prepared by the process according to the invention is important in that this compound may serve as a starting material in the preparation of ε-caprolactam, caprolactone or adipic acid.

The invention will now be elucidated with reference to the following non-limiting examples.

The "unpurified methyl 3-pentenoate" mentioned in the examples (hereafter referred to as unpurified pentenoate) contained approx. 25,000 ppm (2.5 mol %) hydroperoxide compounds. The hydroperoxide compounds were removed by distilling 300 ml of methyl 3-pentenoate in a batch set-up to which 20 g of triphenylphosphine had been added. The methyl 3-pentenoate obtained was stored together with 10 g of 2,4,6-tri-tert-butylphenol and redistilled immediately before use, the hydroperoxide content of the methyl 3-pentenoate so obtained (hereafter referred to as freshly distilled pentenoate) being lower than 40 ppm. Furthermore some hydroperoxide containing mixtures were prepared in the following manner:

Mixture I

In a 100 ml glass vessel freshly distilled methyl 3-pentenoate containing 0.02 mol % methyl cis 2-pentenoate was stirred at room temperature in the presence of air. After 4 days 1 mol % of hydroperoxide was formed (12000 ppm). The analysis was performed by KI-titration in the following manner: To 75 ml of acetic acid/chloroform (2:1 v/v) approximately 1 gram of olefin was added, followed by 5 ml of an aqueous potassium iodide solution (65 g/100 ml). The solution was placed in the dark for half an hour and after the addition of 100 ml of water, titrated with a sodium thiosulphate solution (2.4 g/100 ml) until the brown/yellow colour had disappeared. Also a blanc analysis (without the addition of olefin) was carried out. Acetic acid, chloroform and water were freed from molecular oxygen. The potassium iodide solution was freshly prepared before used.

Mixture II

The procedure for mixture I was repeated with methyl trans 2-pentenoate. After 7 days no detectable hydroperoxide formation was measured. After 15 days 0.1% (1200 ppm) of the starting methyl 2-trans-pentenoate was converted to a equimolar mixture of hydroperoxide compound (I) and (II).

Mixture III

The procedure for mixture I was repeated with methyl cis 2-pentenoate. After 5 days 15–20% of the methyl cis 2-pentenoate was converted to hydroperoxides mixture in a molar ratio for hydroperoxide compounds (I), (II) and (III) of 1:1:3, with a total hydroperoxide content of 18000 ppm.

Mixture IV

The procedure for mixture I was repeated with a mixture of cis and trans 2-hexene. After 5 days 0.035 mol % of hydroperoxyde compounds were formed.

The procedures for preparing mixture I–III demonstrate the higher reactivity for hydroperoxide formation of an alkyl cis 2-pentenoate compared to other alkyl pentenoates.

These experiments also demonstrate that the formation of hydroperoxide compounds can be significant when the reaction (or residence) time is high enough and alkyl cis 2-pentenoate and oxygen are present.

EXAMPLE I

A 150-ml Hastalloy-C steel autoclave (Parr) was filled under nitrogen with 3.87 mg of Rh(acac)(CO)$_2$ (acac= acetylacetonate) (1.5×10$^{-5}$ mol), 37.5×10$^{-5}$ mol phosphite according to formula VI (ligand/rhodium ratio (L/Rh)= 25 mol/mol)) and 40 ml of toluene. Hereafter, the autoclave was closed and purged with nitrogen. Next, the autoclave was brought to a pressure of 1 MPa using carbon monoxide/hydrogen (1:1) and heated to 90° C. in approx. 30 min. Subsequently, a mixture of 3.4 g of freshly distilled methyl 3-pentenoate, 1.0 gram of nonane topped up to 10 ml with toluene was injected into the autoclave. The composition of the reaction mixture was determined by gas chromatography. The results, including the percentage of ligand that had decomposed to catalytically inactive compounds, are listed in Table 1.

The gas chromatography was performed in the following manner: At regular intervals samples were taken and analyzed (column: CP-Sil 8 CB 25 m×0.25 mm Chrompack; temperature progam 60° C., 15 min isothermal than 10° C./min to 140° C. and 5 min isothermal and than 20° C./min to 280° C. and 20 min isothermal. Reaction products were identified by comparison with authenthic samples and by gaschromatography and mass spectrometry (GC/MS).

Comparative Example A

Example I was repeated using unpurified methyl pentenoate. The results are listed in Table 1.

TABLE 1

| Example/ Experiment | Time (h) | Conversion (%) | TOF (h$^{-1}$) | decomposed ligand (%) |
|---|---|---|---|---|
| I | 6 | 30.5 | 99.9 | 5 |
|   | 28.5 | 88.2 | 60.9 | 13 |
| A | 6 | 11.2 | 37.3 |   |
|   | 28.5 | 44.3 | 31.1 | 86 |

Conversion percentage converted methyl 3-pentenoate
TOF Turnover frequency = mol converted methyl 3-pentenoate per mol rhodium per hour

EXAMPLE II

Example I was repeated using 23.0 grams of freshly distilled methyl pentenoate. The results are listed in Table 2.

Comparative Example B

Example I was repeated using unpurified methyl 3-pentenoate (of Example A). The results are listed in Table 2.

TABLE 2

| Example/ Experiment | Time (h) | Conversion (%) | Sel. (%) | n/iso | TOF (h$^{-1}$) | decomposed ligand (%) |
|---|---|---|---|---|---|---|
| II | 2 | 17.5 | 79.5 | 5.17 | 1128.9 |   |
|   | 21 | 82.2 | 77.1 | 4.37 | 503.8 | 13 |
| B | 1.5 | 6.7 | 74.9 | 4.15 | 642.8 |   |
|   | 22 | 10.4 | 68.5 | 2.60 | 67.9 | 95 |

Sel. mol % 5-formylvalerate relative to all products formed (=3-, 4-, 5-formylvalerate and methylvalerate).
n/iso ratio of (5-formylvalerate)/(3- + 4- formylvalerate)

decomposed ligand is calculated as the percentage of the ligands which is decomposed relative to the original amount of ligand at time is 0.

EXAMPLE III

Example I was repeated using 7.5×10$^{-5}$ mol phosphite according to formula VII (L/Rh= 5). The reaction mixture was analyzed after 7 and 25.5 hours. The results are listed in Table 3.

Comparative Experiment C

Example I was repeated using unpurified methyl pentenoate. The results are listed in Table 3.

EXAMPLE IV

A mixture of unpurified methyl 3-pentenoate (12.4 g), methyl 4-pentenoate (12.5 g), methyl cis 2-pentenoate (2.5 mg) and 1 ml n-nonaan in 30 ml toluene (containing 12500 ppm hydroperoxide compounds) was washed 2 times with a an equal volume of a solution containing 2.0 mmol tris(m-sulfonatophenyl)phosphine as sodium salt in water. After separation of the layers the organic layer contained less than 40 ppm hydroperoxide compounds.

A 150 ml Hastalloy-C autoclave (Parr) was filled under nitrogen 0.05 mmol Rh(acac)(CO)$_2$ and 30 ml of a solution containing 2.1 mmol tris(m-sulfonatophenyl)phosphine as sodium salt in water. The autoclave was closed and flushed with nitrogen. Afterwards the autoclave was heated to 110° C. and subsequently pressurized to 1.0 MPa with H$_2$/CO (1/1 mol/mol). Subsequently the obtained pentenoate ester mixture (the organic layer described above) was injected in the autoclave. After 45 minutes the hydroformylation reaction was stopped (79.4% conversion of the methyl 4-pentenoate). No loss of the tris(m-sulfonatophenyl)phosphine ligand was observed.

Comparative experiment D

Example IV was repeated except that the unpurified pentenoate ester containing mixture was not washed with the aqueous solution (the hydroperoxide compounds were thus not removed). After 60 minutes the hydroformylation reaction was stopped. 57.4% conversion of the methyl 4-pentenoate was observed. Using 31P NMR it was found that 43.8% of the ligand was oxidized to catalytically inactive compounds.

TABLE 3

| Example/ Experiment |   | Time (h) | Conversion (%) | Selectivity (%) | n/iso | TOF (h$^{-1}$) |
|---|---|---|---|---|---|---|
| III | Freshly | 7 | 11.3 | 83.3 | 9.16 | 31.5 |
|   | distilled | 25.5 | 41.4 | 84.9 | 11.6 | 31.7 |
|   | pentenoate |   |   |   |   |   |
| C | Unpurified | 7 | 7.8 | 81.4 | 7.2 | 17.6 |

We claim:

1. A process for the preparation of a 5-formylvalerate ester comprising the step of hydroformylating a mixture of pentenoate esters in the presence of a catalyst system, wherein the mixture of pentenoate esters contains less than 500 ppm of hydroperoxide compounds and the catalyst system comprises a metal from groups 8–10 of the Periodic Table of Elements and a ligand containing a mono- or multidentate organic phosphorous ligand.

2. A process according to claim 1, wherein said mixture of pentenoate esters contains less than 100 ppm of hydroperoxide compounds.

3. A process according to claim 1 or 2, wherein the mixture of pentenoate esters comprises cis 2-pentenoate ester.

4. A process according to claim 1 or 2, wherein said process is performed continuously and wherein said process comprises the further step of recycling at least a portion of any pentenoate esters remaining unconverted following said hydroformylation as starting compounds to said hydroformulation step.

5. A process according to claim 1 or 2, wherein said process comprises the further step of passing the pentenoate ester mixture over alumina before conducting said hydroformylating.

6. A process according to claim 1, wherein said process is performed continuously, the said mixture of pentenoate esters comprises cis 2-pentenoate ester, and said process comprises the further step of recycling at least a portion of any pentenoate esters remaining unconverted following said hydroformylation as starting compounds to said hydroformulation step.

7. A process according to claim 6, wherein said process comprises the further step of passing said pentenoate ester mixture over alumina before conducting said hydroformylating.

8. A process according to claim 1, 2, 6 or 7 wherein in said catalyst system said metal is a group 8 metal, and said phosphorous ligand and said group 8 metal are present in a molar ratio of greater than 2:1.

9. A process according to claim 1, 2, 6, or 7, wherein said metal is cobalt, ruthenium, iridium or rhodium.

10. A process according to claim 1, 2, 6, or 7, wherein in said catalyst system said phosphorous ligand is represented by the formula:

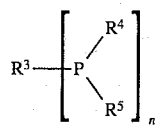

wherein n is 1–6, in which when n is 1, $R^3$, $R^4$ and $R^5$ are the same or different monovalent organic groups in which the organic group is —Y, —O—Y, —N($R^6$)—Y or —S—Y or $R^4$ and $R^5$ form one divalent organic group in which divalent organic group is —Y—, —O—Y—O—, —O—Y—, —O—Y— N($R^6$)— or —N($R^6$)—Y—N($R^7$)— and $R^3$ is a monovalent group as defined above and in which Y is a monovalent or divalent organic group having 1–20 carbon atoms and $R^6$ and $R^7$ are individually hydrogen or an organic group having 1 to 12 carbon atoms, and in which for n is 2–6, $R^3$ is a multivalent organic bridging group having 1–30 carbon atoms and $R^4$ and $R^5$ can be the same or different monovalent groups as defined above and/or $R^4$ and $R^5$ form one divalent group as defined above.

11. A process according to claim 1, wherein said catalyst system said phosphorous ligand and said metal are present in a molar ratio of greater than 2:1, said metal is cobalt, ruthenium, iridium or rhodium, and said phosphorous ligand is represented by the formula:

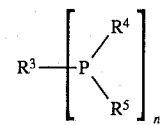

wherein n is 1–6, in which when n is 1, $R^3$, $R^4$ and $R^5$ are the same or different monovalent organic groups in which the organic group is —Y, —O—Y, —N($R^6$)—Y or —S—Y or $R^4$ and $R^5$ form one divalent organic group in which divalent organic group is —Y—, —O—Y—O—, —O—Y—, —O—Y—N($R^6$)— or —N($R^6$)—Y—N($R^7$)— and $R^3$ is a monovalent group as defined above and in which Y is a monovalent or divalent organic group having 1–20 carbon atoms and $R^6$ and $R^7$ are individually hydrogen or an organic group having 1 to 12 carbon atoms, and in which for n is 2–6, $R^3$ is a multivalent organic bridging group having 1–30 carbon atoms and $R^4$ and $R^5$ can be the same or different monovalent groups as defined above and/or $R^4$ and $R^5$ form one divalent group as defined above.

12. A process according to claim 11, wherein the mixture of pentenoate esters comprises cis 2-pentenoate ester.

13. A process according to 11 or 12, wherein said process is performed continuously and wherein said process further comprises a recycling step in which at least a portion of any pentenoate esters remaining unconverted following said hydroformylation are recycled as starting compounds to said hydroformulation step.

14. A process according to claim 11 or 12, wherein said process further comprises passing the pentenoate ester mixture over alumina before conducting said hydroformylating.

15. A process according to claim 11, wherein said mixture of pentenoate esters contains less than 100 ppm of hydroperoxide compounds.

16. A process according to claims 11, 12 or 15, wherein said process further comprises reducing the hydroperoxide content of the pentenoate ester mixture before conducting said hydroformylating.

* * * * *